United States Patent
Danacioglu et al.

(10) Patent No.: US 9,034,043 B2
(45) Date of Patent: May 19, 2015

(54) INTERVERTEBRAL IMPLANT AND INSERTION INSTRUMENT

(75) Inventors: Fatih U. Danacioglu, Ridgewood, NJ (US); Jason P. Bulaclac, Sparta, NJ (US)

(73) Assignee: Zimmer Spine, Inc., Minneapolis, MN (US)

( * ) Notice: Subject to any disclaimer, the term of this patent is extended or adjusted under 35 U.S.C. 154(b) by 709 days.

(21) Appl. No.: 13/366,060

(22) Filed: Feb. 3, 2012

(65) Prior Publication Data

US 2013/0204370 A1 Aug. 8, 2013

(51) Int. Cl.
*A61F 2/44* (2006.01)
*A61F 2/46* (2006.01)
*A61F 2/28* (2006.01)
*A61F 2/30* (2006.01)

(52) U.S. Cl.
CPC ............ *A61F 2/4611* (2013.01); *A61F 2/442* (2013.01); *A61F 2/447* (2013.01); *A61F 2002/2835* (2013.01); *A61F 2002/30158* (2013.01); *A61F 2002/30261* (2013.01); *A61F 2002/30772* (2013.01); *A61F 2002/30785* (2013.01); *A61F 2002/30904* (2013.01); *A61F 2002/4475* (2013.01); *A61F 2002/448* (2013.01); *A61F 2002/4622* (2013.01); *A61F 2002/4627* (2013.01); *A61F 2002/4628* (2013.01); *A61F 2230/0026* (2013.01); *A61F 2230/0082* (2013.01)

(58) Field of Classification Search
USPC ...................................... 606/17.11, 17.16, 99
See application file for complete search history.

(56) References Cited

U.S. PATENT DOCUMENTS

| 5,443,514 | A | 8/1995 | Steffee |
| 5,782,830 | A | 7/1998 | Farris et al. |
| 6,319,257 | B1 | 11/2001 | Carignan et al. |
| 6,610,065 | B1 | 8/2003 | Branch et al. |
| 7,901,458 | B2 | 3/2011 | DeRidder et al. |
| 7,938,857 | B2 | 5/2011 | Garcia-Bengochea et al. |
| 2003/0149438 | A1 | 8/2003 | Nichols et al. |
| 2004/0162616 | A1 | 8/2004 | Simonton et al. |
| 2005/0027360 | A1 | 2/2005 | Webb et al. |
| 2008/0172127 | A1* | 7/2008 | Perez-Cruet et al. ...... 623/17.16 |
| 2008/0288076 | A1 | 11/2008 | Soo et al. |
| 2009/0030423 | A1 | 1/2009 | Puno |
| 2009/0248163 | A1 | 10/2009 | King et al. |

(Continued)

FOREIGN PATENT DOCUMENTS

| EP | 0646366 A1 | 4/1995 |
| EP | 1905391 B1 | 1/2010 |

(Continued)

*Primary Examiner* — Christian Sevilla
(74) *Attorney, Agent, or Firm* — Seager, Tufte & Wickhem, LLC

(57) ABSTRACT

An intervertebral implant and associated insertion instrument. The intervertebral implant includes an instrument engagement interface including first and second channels extending along opposite sides of the implant forwardly from a trailing end wall of the implant and a positioning projection extending rearward from the trailing end wall of the implant. The insertion instrument includes a grasping mechanism for engagement with the instrument engagement interface. The grasping mechanism includes first and second jaws including grasping portions positionable in the first and second channels and an enlarged opening defined between the first and second jaws for receiving the positioning projection therein.

10 Claims, 9 Drawing Sheets

(56) References Cited

U.S. PATENT DOCUMENTS

| | | | |
|---|---|---|---|
| 2010/0152853 A1* | 6/2010 | Kirschman | 623/17.11 |
| 2010/0249795 A1 | 9/2010 | Dimauro et al. | |
| 2011/0106259 A1 | 5/2011 | Lindenmann et al. | |
| 2011/0295372 A1 | 12/2011 | Peterman et al. | |

FOREIGN PATENT DOCUMENTS

| | | |
|---|---|---|
| WO | 03/053290 A1 | 7/2003 |
| WO | 2004112660 A1 | 12/2004 |
| WO | 2007070751 A1 | 6/2007 |

* cited by examiner

INTERVERTEBRAL IMPLANT AND INSERTION INSTRUMENT

TECHNICAL FIELD

The disclosure is directed to an intervertebral implant and an instrument configured to assist inserting the intervertebral implant between vertebrae. More particularly, the disclosure is directed to an insertion instrument configured to interface with and grasp an intervertebral implant.

BACKGROUND

A damaged or degenerated intervertebral disc between adjacent vertebrae may prompt spinal surgery to alleviate pain or otherwise stabilize the vertebral segment. During a spinal fixation procedure, an intervertebral implant may be inserted within a space created by the removal or partial removal of an intervertebral disc between adjacent vertebrae. The intervertebral implant may maintain the proper spacing and/or lordosis between vertebrae and restore stability to the spine. Subsequent bone growth may fuse the implant to the adjacent vertebrae to provide further stabilization.

An intervertebral implant may be inserted during a spinal fixation procedure using an anterior, lateral, posterior, antero-lateral, postero-lateral, translateral, oblique or transforaminal approach, or other desired approach, for example. An insertion instrument may be used to facilitate insertion of the intervertebral implant in the disc space between the vertebrae. Accordingly, there is an ongoing need to provide alternative intervertebral implants and associated insertion instruments to install the intervertebral implants.

SUMMARY

The disclosure is directed to several alternative designs, materials and methods of manufacturing intervertebral implants and associated insertion instruments and assemblies, and uses thereof.

Accordingly, one illustrative embodiment is an intervertebral implant configured for insertion between adjacent vertebrae. The implant includes a leading end portion, a trailing end portion, a superior surface configured to engage a first vertebra, an inferior surface configured to engage a second vertebra, a first side surface, and a second side surface opposite the first side surface. The implant further includes an insertion instrument interface including a first channel extending along the first side surface from a trailing end wall toward the leading end, a second channel extending along the second side surface from the trailing end wall toward the leading end, and a positioning projection extending rearward from the trailing end wall. The first channel has a base wall and the second channel has a base wall, wherein a width of the intervertebral implant between the base wall of the first channel and the base wall of the second channel is less than a width of the positioning projection.

Another illustrative embodiment is an insertion instrument for installing an intervertebral implant between first and second vertebrae. The insertion instrument includes an inner shaft having a proximal end and a distal end, an outer shaft having a proximal end and a distal end with the outer shaft slidably disposed over the inner shaft, and a grasping mechanism at the distal end of the inner shaft configured to grasp a trailing end of an intervertebral implant. The grasping mechanism includes first and second jaws configured to converge toward each other upon axial movement of the outer shaft relative to the inner shaft to grasp the trailing end of an intervertebral implant therebetween. The first jaw includes a grasping portion extending to a free distal end of the first jaw configured for engaging along a first side surface of the intervertebral implant, and the second jaw includes a grasping portion extending to a free distal end of the second jaw configured for engaging along a second side of the intervertebral implant. The grasping mechanism further defines an enlarged opening between the first jaw and the second jaw. The enlarged opening is located proximal of the grasping portions of the first and second jaws. The enlarged opening has a width larger than a width measured between the grasping portions of the first and second jaws.

Yet another illustrative embodiment is an assembly for installing an intervertebral implant between first and second vertebrae. The assembly includes an intervertebral implant and an insertion instrument configured to be removably coupled to the intervertebral implant. The intervertebral implant includes a leading end portion, a trailing end portion, a superior surface configured to engage a first vertebra, an inferior surface configured to engage a second vertebra, a first side surface, and a second side surface opposite the first side surface. The intervertebral implant also includes a first channel extending along the first side surface from a trailing end wall toward the leading end and a second channel extending along the second side surface from the trailing end wall toward the leading end. The intervertebral implant further includes a positioning projection extending rearward from the trailing end wall. The insertion instrument includes an elongate shaft extending from a handle portion to a grasping mechanism configured to grasp the intervertebral implant. The grasping mechanism includes first and second jaws configured to grasp the trailing end portion of the intervertebral implant therebetween. The first jaw includes a grasping portion positionable in the first channel along the first side surface of the intervertebral implant and the second jaw includes a grasping portion positionable in the second channel along the second side surface of the intervertebral implant. The positioning projection is positionable in an enlarged opening defined between the first jaw and the second jaw when the grasping portions of the first and second jaws are positioned in the first and second channels.

The above summary of some example embodiments is not intended to describe each disclosed embodiment or every implementation of the aspects of the disclosure.

BRIEF DESCRIPTION OF THE DRAWINGS

The aspects of the disclosure may be more completely understood in consideration of the following detailed description of various embodiments in connection with the accompanying drawings, in which.

Figure 1:
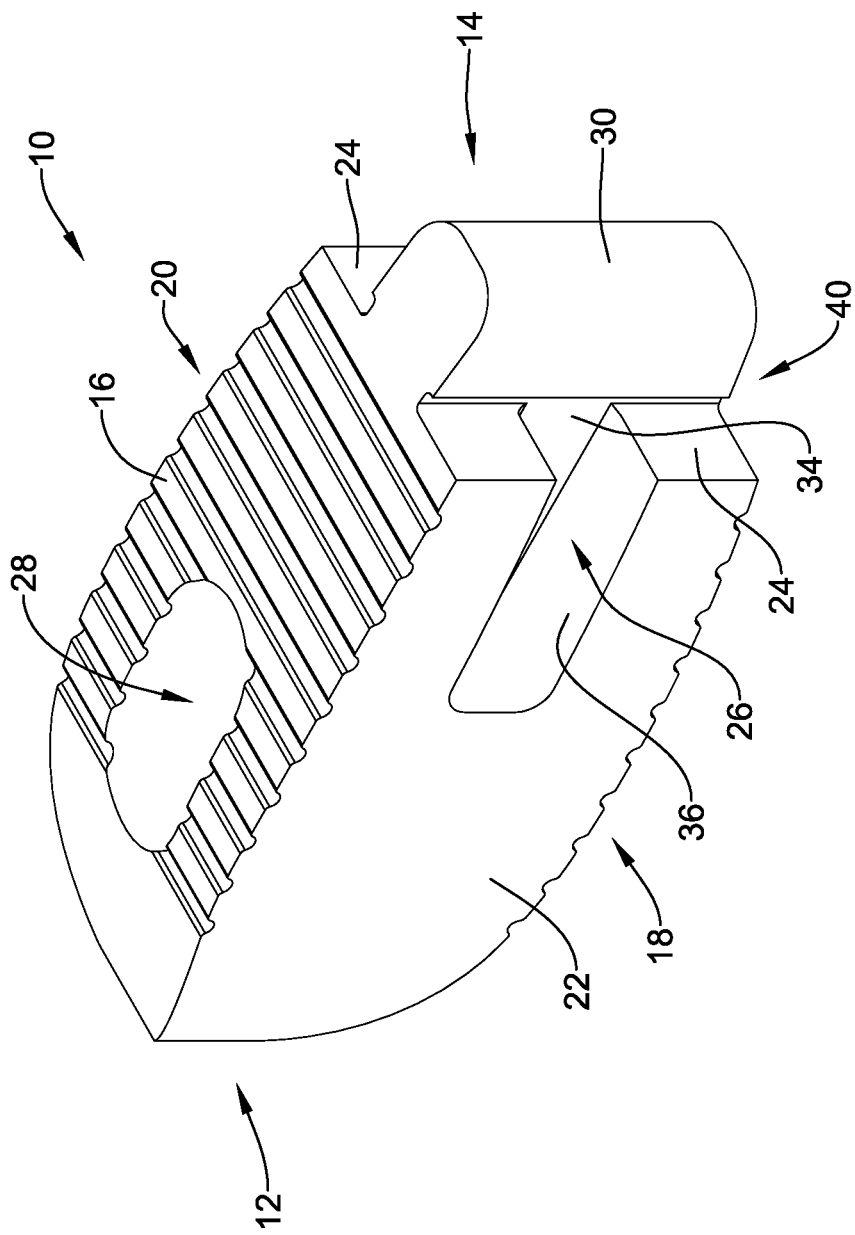
FIG. 1 is a perspective view of an exemplary intervertebral implant in accordance with this disclosure.

While the aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure. The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

Figure 2:
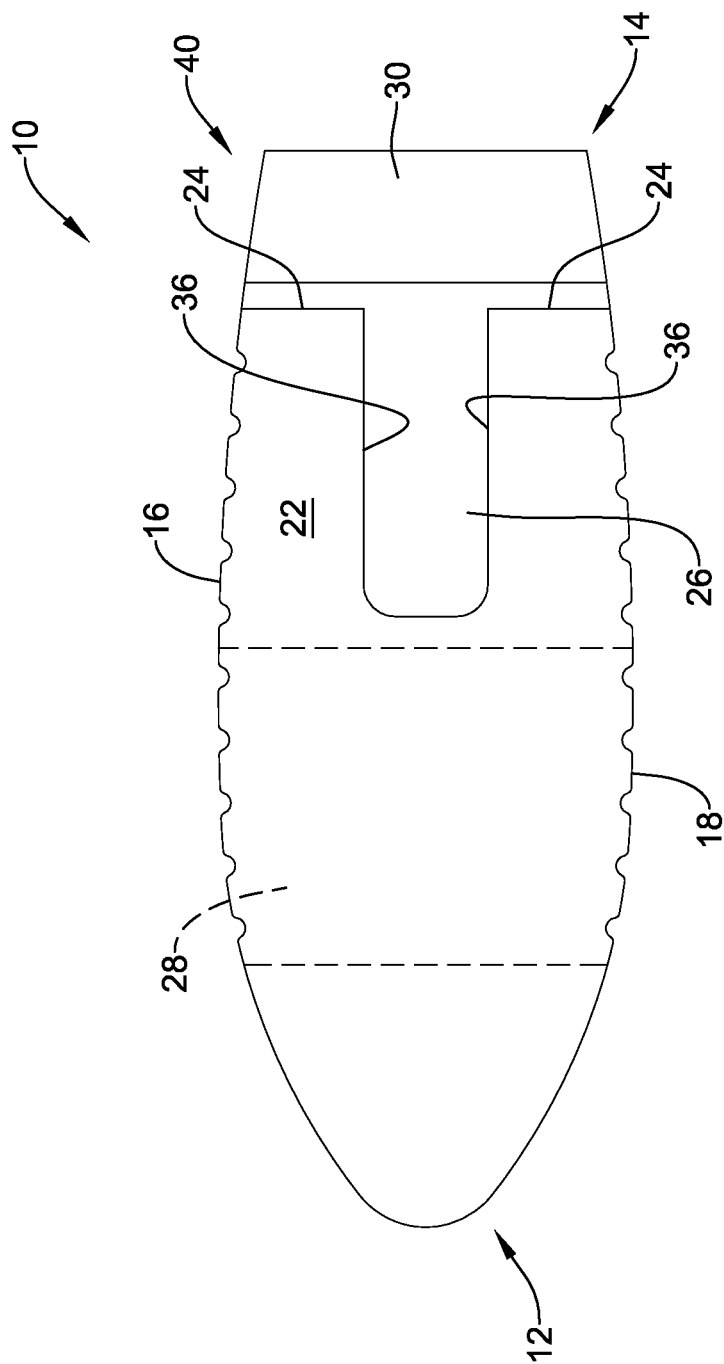
FIG. 2 is a side view of the intervertebral implant of FIG. 1.
Figure 3:
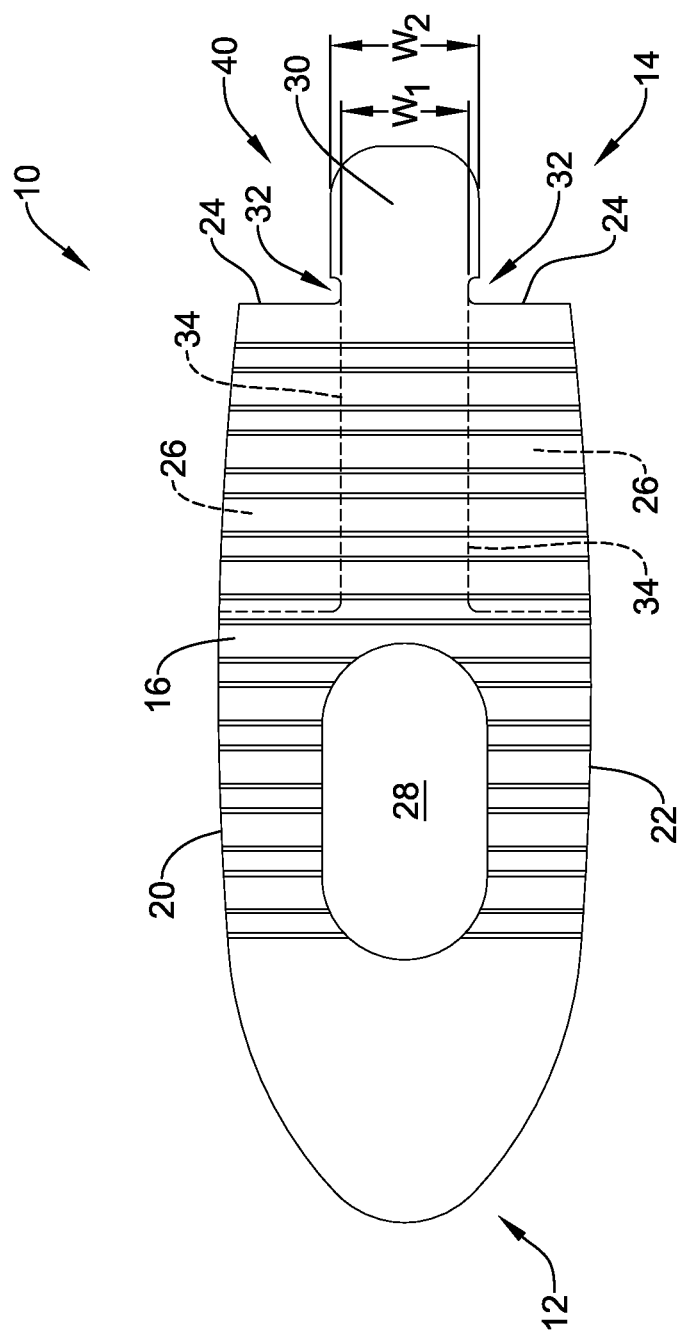
FIG. 3 is a top view of the intervertebral implant of FIG. 1.

An exemplary intervertebral implant 10 for placement in a disc space between adjacent vertebrae during a spinal fixation procedure is shown at FIG. 1. FIGS. 2 and 3 illustrate top and side views, respectively, of the implant 10.

The implant 10 may be formed of a biologically compatible material sufficient to withstand compressive spinal loads. In some instances, the implant 10 may be formed of a porous metal defining a plurality of pores formed by a metallic scaffold. For instance, the porous metal material may be tantalum, titanium, zirconium, cobalt, chrome and stainless steel, or alloys thereof. In some instances, the pores of the porous metal will have a pore size of about 150 microns to about 500 microns, or more. However, in other instances a smaller pore size may be desired, such as a pore size of less than about 150 microns. The open cell structure of the porous metal scaffold of the implant 10 may mimic the microstructure of a natural cancellous bone, acting as an osteoconductive matrix for the incorporation of bone, providing optimal permeability and high surface area to encourage new bone in-growth into the pores of the implant 10. Furthermore, the porous metal material may have an elastic modulus similar to natural cancellous bone. For instance, depending on its porosity, the porous metal may have an elastic modulus of about 1.5 GPa to about 4 GPa, or about 3 GPa, whereas natural cancellous bone, depending on physiological factors of a specific patient, may have an elastic modulus of about 0.1 GPa to about 3 GPa, or about 0.5 GPa in many instances.

One exemplary porous metal is Trabecular Metal™ material, which is a porous tantalum material marketed by Zimmer Spine, Inc. of Minneapolis, Minn. This material is also disclosed in several U.S. patents, including, for example, U.S. Pat. Nos. 5,282,861, 5,443,515, and 6,063,442, the disclosures of which are incorporated herein by reference. These patents describe the formation of a tantalum porous structure by chemical vapor deposition of tantalum onto a foam carbon structure.

In other embodiments, the implant 10 may be formed of a polymeric material, such as a thermoplastic polymeric material. Some examples of suitable thermoplastic polymeric materials include polyether ether ketone (PEEK), ultra-high molecular weight polyethylene (UHMWPE), poly(methyl methacrylate) (PMMA), polyethylene terephthalate (PET), and mixtures or blends thereof. Other suitable polymeric materials include thermoplastic elastomers such as polyurethanes and mixtures or blends thereof. In still other embodiments, the implant 10 may be formed of a metallic material, such as titanium or stainless steel, for example.

The implant 10 may include a leading end 12, and an opposite trailing end 14, in which the leading end 12 may be configured to be inserted into the disc space with the leading end 12 first. Accordingly, the leading end 12 may be configured with a tapered or curved nose to facilitate insertion between the vertebrae.

The implant 10 may also include an upper, superior surface 16 extending between the leading end 12 and the trailing end 14, and a lower, inferior surface 18 extending between the leading end 12 and the trailing end 14. The upper surface 16 and/or lower surface 18 may be a tapered, curved or arcuate, or flat surface as desired to conform to the end plates of the vertebrae and the intervertebral space such that the upper surface 16 and/or lower surface 18 sufficiently bears against the end plates of the vertebrae to support spinal loading. The upper surface 16 and/or lower surface 18 may be a discontinuous surface intended to contact the end plates of the vertebrae to resist migration of the implant 10 between the adjacent vertebrae. For example, the upper surface 16 and/or the lower surface 18 may include a plurality of recesses, ridges, grooves, teeth, surface roughening or other features to increase the stability and/or securement of the spinal implant between the vertebrae. As shown in the figures, the upper surface 16 and the lower surface 18 may include semicircular grooves extending across the implant 10 between the side surfaces 20, 22. The semicircular grooves may be spaced apart by flat portions of the upper and lower surfaces 16, 18. In some instances the migration resistance of the spinal implant 10 may be attributed, at least in part to the coefficient of friction of the material of the spinal implant 10. For instance, a spinal implant 10 formed of a porous tantalum metal, or other porous material, may have abrasive or rough exterior surfaces for contacting the vertebrae.

The implant 10 may also include a first side surface 20 and a second side surface 22 extending between the leading end 12 and the trailing end 14 of the implant 10. The side surfaces 20, 22, which may extend from the upper surface 16 to the lower surface 18, may define the height of the implant 10.

As illustrated, the implant 10 may include a cavity 28 extending into or through the implant 10. For example, a cavity 28 may extend between the superior surface 16 and the inferior surface 18. In other instances, the cavity 28 may be oriented in a different direction, if desired. Additionally or alternatively, the implant 10 may include one or more cavities extending between the side surfaces 20, 22. The cavity 28 may be configured to be filled with bone growth material prior to implanting the implant 10 between adjacent vertebrae. The bone growth material may facilitate bone growth and fusion between the adjacent vertebrae. In some embodiments, a plurality of cavities 28 may be present to receive bone growth material. Example materials may include demineralized bone, Bone Morphogenic Proteins (e.g. BMP-2 or BMP-7), a patient's own bone marrow, or other suitable material.

The trailing end 14 of the implant 10 may include an instrument engagement interface 40 configured to mate with an implant engagement interface of an insertion instrument, as will be further described herein. The instrument engagement interface 40 may ensure that the implant 10 is properly and securely coupled to an insertion instrument during insertion of the implant 10 into the prepared disc space between adjacent vertebrae.

The instrument engagement interface 40 of the implant 10 shown in FIG. 1 includes a first elongate channel 26 extending into the implant 10 from the first side surface 20 of the implant 10 on the first side of the implant 10, and a second elongate channel 26 extending into the implant 10 from the second side surface 22 of the implant on the second side of the implant 10, as shown in FIG. 3. The first and second elongate channels 26 may extend from a trailing end wall 24 at the trailing end 14 of the implant 10 toward the leading end 12 of the implant 10. The elongate channels 26 may be defined by a base wall 34 at the base of the elongate channel 26 extending between parallel side walls 36. The elongate channels 26 may be configured to receive the prongs or jaws of an insertion instrument in a direction generally parallel to and between the parallel side walls 36.

The instrument engagement interface 40 of the implant 10 may also include a positioning projection 30 extending rearwardly from the trailing end wall 24 of the implant 10. The positioning projection 30 may be configured to be received in an enlarged opening between the prongs of an insertion instrument to facilitate confirmation of proper securement of the implant 10 between the prongs of the insertion instrument. The positioning projection 30 may extend from the upper surface 16 to the lower surface 18, or any desired portion thereof, with a portion of the positioning projection 30 located rearwardly of the channels 26 which extend forwardly of the trailing end wall 24.

The width of the positioning projection 30 may be sized larger than the distance between the base walls 34 of the channels 26, forming a notch or ledge 32 extending in a superior-inferior direction at the base of the positioning projection 30 (i.e., where the positioning projection 30 extends from the body of the implant 10 at the trailing end wall 24. As shown in FIG. 3, a width W1 of the implant 10 measured between the base wall 34 of the first elongate channel 26 and the base wall 34 of the second elongate channel 26 may be less than the width W2 of the positioning projection 30 extending rearwardly from the trailing end wall 24 of the implant 10. The notches or ledges 32 are thus formed proximate the trailing end wall 24 to form the dimensional change.

Figure 4:
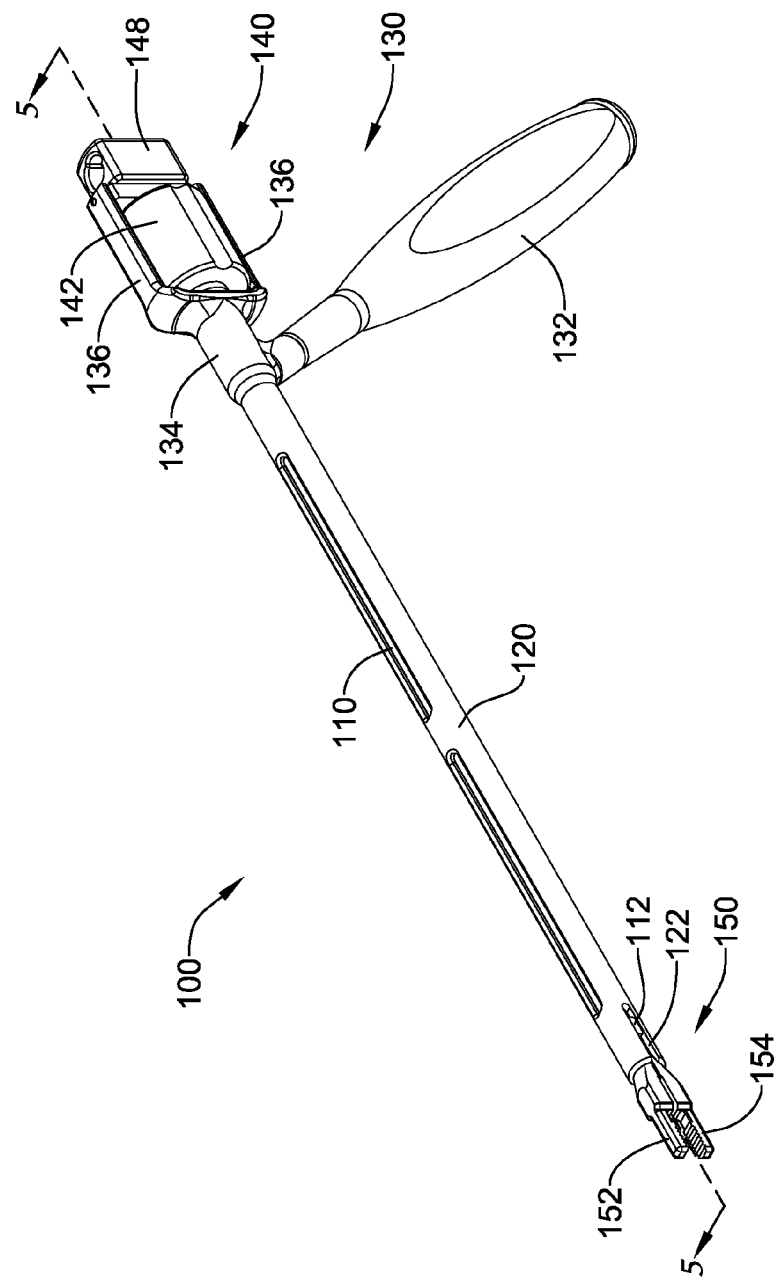
FIG. 4 is a perspective view of an exemplary insertion instrument for inserting the intervertebral implant of FIG. 1 in a disc space between adjacent vertebrae.

The intervertebral implant 10 may be configured to be inserted during a spinal fixation procedure using any desired approach, such as an anterior, lateral, posterior, antero-lateral, postero-lateral, translateral, oblique or transforaminal approach. An insertion instrument may be used to facilitate insertion of the intervertebral implant in the disc space between the vertebrae. One illustrative insertion instrument 100 configured for mating with the implant 10 is illustrated in FIG. 4.

The insertion instrument 100 may include a first elongate shaft and a second elongate shaft extending along the first elongate shaft and axially translatable relative to the first elongate shaft. For example, the first elongate shaft may be an inner shaft 110 and the second elongate shaft may be an outer shaft 120 coaxially surrounding the inner shaft 110. The outer shaft 120 may be slidably disposed over the inner shaft 110, providing relative axial translation of the inner shaft 110 through the lumen of the outer shaft 120.

The insertion instrument 100 may include a handle assembly 130 including a handle 132 extending from a housing 134. The handle 132 may be configured to be grasped by a user to control movement of the insertion instrument 100 during insertion of the implant 10 into a disc space during a medical procedure.

The housing 134, which may be fixedly attached to the outer shaft 120 or formed as a unitary member with the outer shaft 120, may include an actuation mechanism 140 configured for generating axial translation of the inner shaft 110 relative to the outer shaft 120. For example, the actuation mechanism 140 may include a rotatable knob 142 which may be rotated by a user to generate axial movement of the inner shaft 110 through the lumen of the outer shaft 120. The rotatable knob 142 may be positioned in an opening of the housing 134 between upper and lower arms 136 which extend between a proximal end wall of the housing 134 and a distal end wall of the housing 134. Accordingly, portions of the rotatable knob 142 may be accessible through the opening on opposing sides of the housing 134 to be manipulated by a user.

Figure 5:
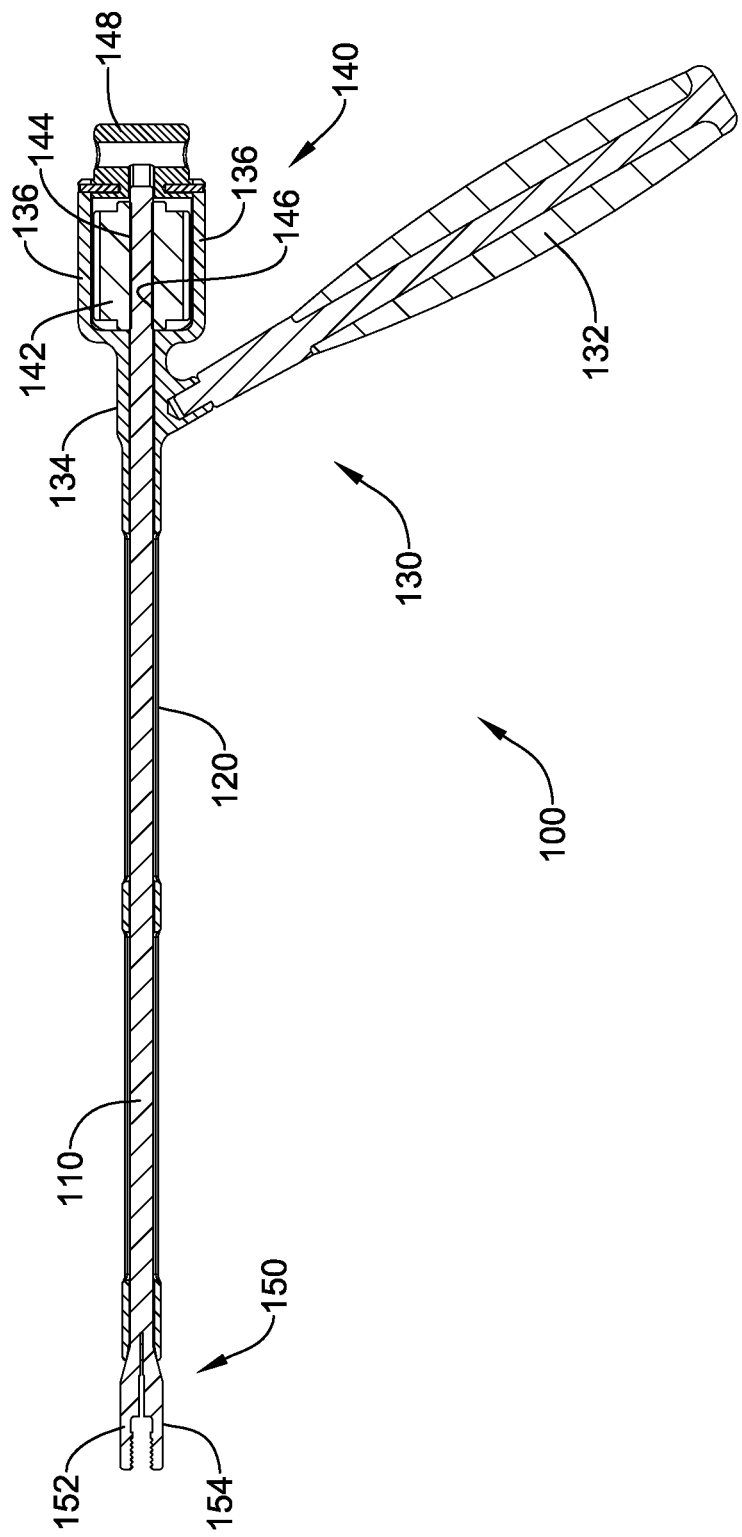
FIG. 5 is a cross-sectional view of the insertion instrument of FIG. 4.

The knob 142 may be rotatably coupled to the inner shaft 110 to convert rotational movement of the knob 142 relative to the outer shaft 120 to axial movement of the inner shaft 110 relative to the outer shaft 120 (e.g., through axial translation of the inner shaft 110 through the lumen of the outer shaft 120). For example, as shown in FIG. 5, a proximal portion of the inner shaft 110 may include a threaded section 144 threadably engaging a threaded section 146 of a bore of the knob 142. For example, the proximal section of the inner shaft 110 may extend through an axial bore of the knob 142 such that a threaded section 144 of the inner shaft 110 threadably mates with the threaded section 146 of the bore of the knob 142. The interaction of the threaded section 144 of the inner shaft 110 with the threaded section 146 of the knob 142 converts rotational movement of the knob 142 about the axis of the inner shaft 110 into axial movement of the inner shaft 110 relative to the knob 142, and thus the outer shaft 120.

The insertion instrument 100 may include a keying feature configured to resist relative rotational movement between the inner shaft 110 and the outer shaft 120. For example, one of the inner shaft 110 and the outer shaft 120 of the insertion instrument 100 may include a tab 112 positioned in a slot 122 of the other of the inner shaft 110 and the outer shaft 120. For instance, the inner shaft 110 may include a tab 112 extending radially outward into a slot 122 formed in the outer shaft 120. The tab 112 may be a unitary portion of the inner shaft 110 or secured to the inner shaft 110 by any desired means. The slot 122 may open out to the distal end 124 of the outer shaft 120 such that the tab 112 may be inserted into the slot 122 in a longitudinal direction from the distal end 124 of the outer shaft 120 as the inner shaft 110 is assembled through the lumen of the outer shaft 120. Once positioned within the slot 122, the tab 112 may contact side surfaces of the slot 122 to prevent relative rotation between the inner shaft 110 and the outer shaft 120 while axially sliding in the slot 122 to permit axial movement of the inner shaft 110 relative to the outer shaft 120.

The handle assembly 130 may also include a striking plate 148 configured to receive striking blows from a mallet or other striking tool during a medical procedure to facilitate placement of the implant 10 between adjacent vertebrae, as desired. The striking plate 148 may be attached to the upper and lower arms 136 of the housing 134 with pins, for example. In other embodiments, the striking plate 148 may be attached to the arms 136 of the housing 134 in another fashion.

In some instances, the striking plate 148 may form the proximal end wall of the housing 134, bounding the knob 142 between the distal end wall of the housing 134 and the striking plate 148. Thus, the knob 142 may be bound by portions of the housing 134 to prevent appreciable axial movement of the knob 142 in the opening of the housing 134 while being rotated. In other words, during rotation of the knob 142 in a first direction, the knob 142 may contact or press against the proximal end wall, and during rotation of the knob 142 in a second, opposite direction, the knob 142 may contact or press against the distal end wall.

The insertion instrument 100 may also include an implant engagement interface, such as a grasping mechanism 150 located at a distal end of the insertion instrument 100 configured to selectively grasp the intervertebral implant 10 for insertion into a disc space during a medical procedure. For example, the grasping mechanism 150 may be located at the distal end of the inner shaft 110, and be configured to grasp a trailing end of the intervertebral implant 10. In some instances, the grasping mechanism 150 may be formed as a unitary distal portion of the inner shaft 110, while in other embodiments the grasping mechanism 150 may be otherwise secured to the distal end of the inner shaft 110.

The grasping mechanism 150 may include a first jaw 152 and a second jaw 154 which may be resiliently deflectable toward and/or away from one another to receive and grasp the trailing end portion of the intervertebral implant 10 therebetween.

Figure 6A:
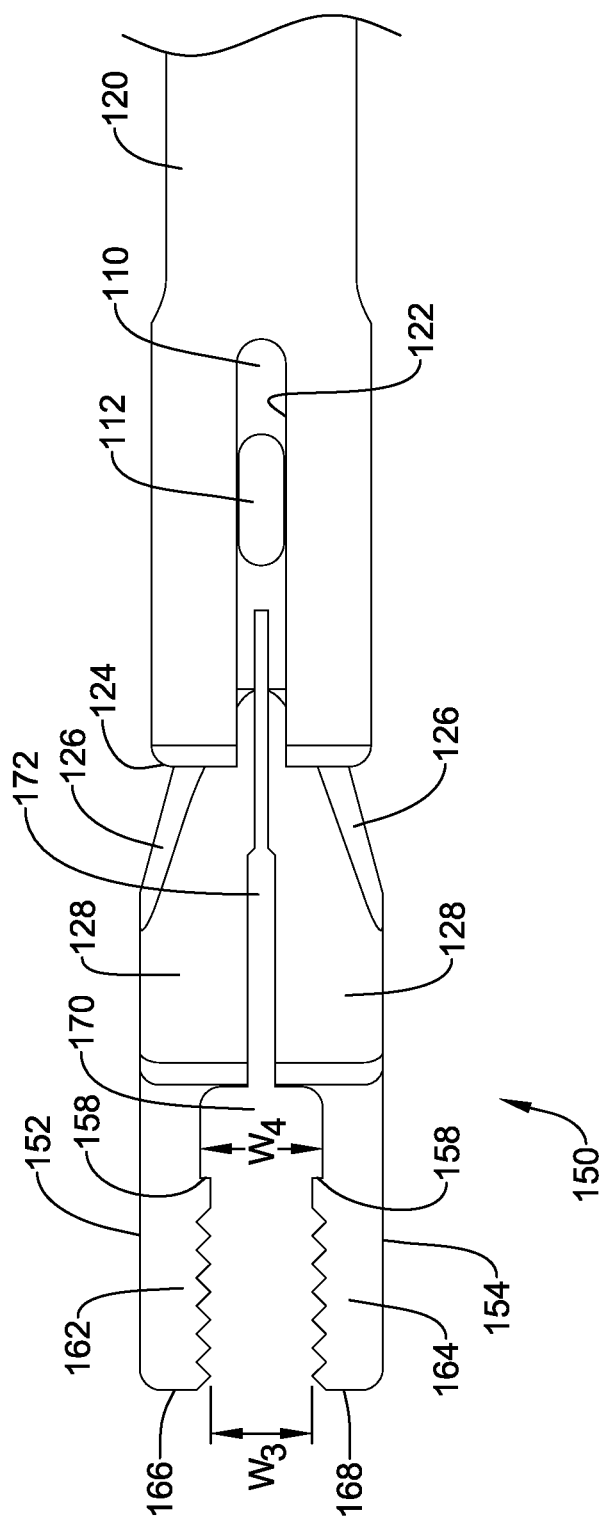
FIGS. 6A and 6B are enlarged views of the grasping mechanism of the insertion instrument of FIG. 4 in a released position and an engaged position, respectively.
Figure 6B:
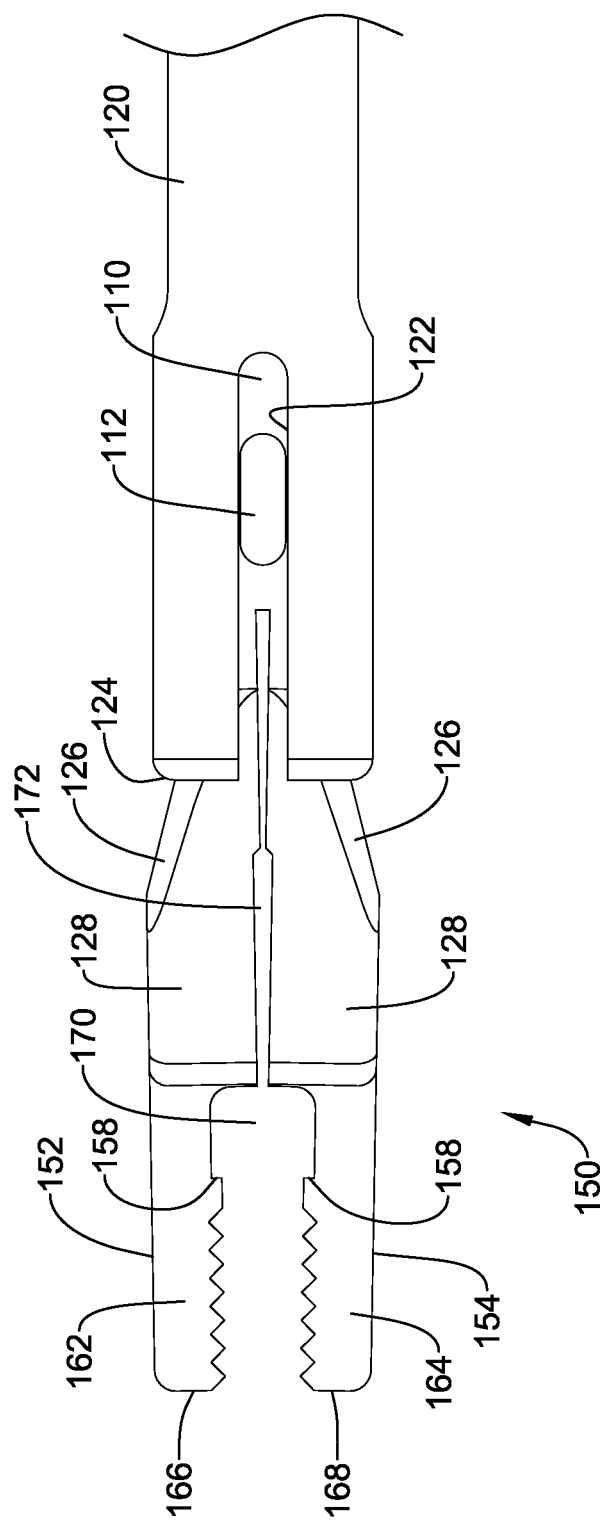

FIGS. 6A and 6B further illustrate features of the grasping mechanism 150 and associated functionality of the insertion instrument 100. FIG. 6A shows the first and second jaws 152, 154 in a first, released configuration in which the jaws 152, 154 are at an equilibrium position. FIG. 6B shows the first and second jaws 152, 154 in a second, grasping configuration in which the jaws 152, 154 are displaced toward one another in a deflected position to grasp the implant 10 therebetween. Actuation of the jaws 152, 154 from the first configuration to the second configuration may be performed by axially translating the inner shaft 110 relative to the outer shaft 120. For example, via rotation of the knob 142, the inner shaft 110 may be translated proximally within the outer shaft 120 such that the distal end 124 of the outer shaft 120 contacts the tapered surfaces 126 of the base portions 128 of the jaws 152, 154, and thus exerts a force against the tapered surfaces 126 to move the first and second jaws 152, 154 toward one another, as shown in FIG. 6B.

The first and second jaws 152, 154 of the grasping mechanism 150 may be sized and configured to securely grasp the implant 10 therebetween. For example, the first jaw 152 may include a grasping portion 162 extending to a free distal end 166 of the first jaw 152 configured for engaging along a first side surface of the intervertebral implant 10 and the second jaw 154 may include a grasping portion 164 extending to a free distal end 168 of the second jaw 154 configured for engaging along a second side of the intervertebral implant 10. In some instances, the grasping portions 162, 164 of the first and second jaws 152, 154 may include teeth, serrations, ridges, etc. for engaging the intervertebral implant 10.

The grasping mechanism 150 may further define an enlarged opening 170 between the first jaw 152 and the second jaw 154 located proximal of the grasping portions 162, 164 of the first and second jaws 152, 154. The enlarged opening 170 may be located between the grasping portions 162, 164 of the first and second jaws 152, 154 and the base portions 128 of the first and second jaws 152, 154. The enlarged opening 170 may have a width W4 larger than a width W3 measured between the grasping portions 162, 164 of the first and second jaws 152, 154. Accordingly, the first and second jaws 152, 154 may include a lip 158 located at the junction between the grasping portions 162, 164 and the enlarged opening 170. The enlarged opening 170 may be configured to receive and retain the positioning projection 30 therein while the grasping portions 162, 164 of the jaws 152, 154 grasp the sides of the implant 10.

The grasping mechanism 150 may include a gap 172 between the base portions 128 of the first jaw 152 and the second jaw 154 which extends proximal of the enlarged opening 170. The gap 172 may permit the base portions 128 of the jaws 152, 154 to move toward one another with the force exerted by the outer shaft 120 to deflect the grasping portions 162, 164 toward one another. The gap 172 may have a width less than the width W4 of the enlarged opening 170.

Figure 7:
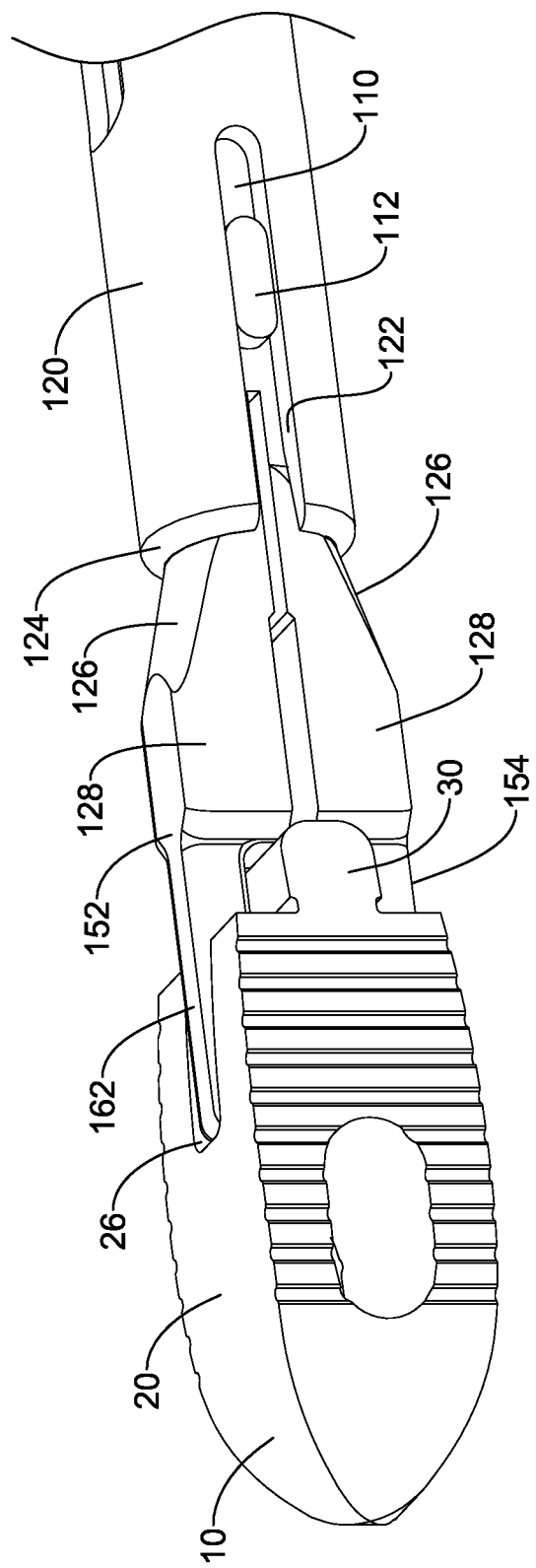
FIG. 7 is a perspective view of the intervertebral implant of FIG. 1 being grasped by the insertion instrument of FIG. 4 for insertion between adjacent vertebrae.
Figure 8:
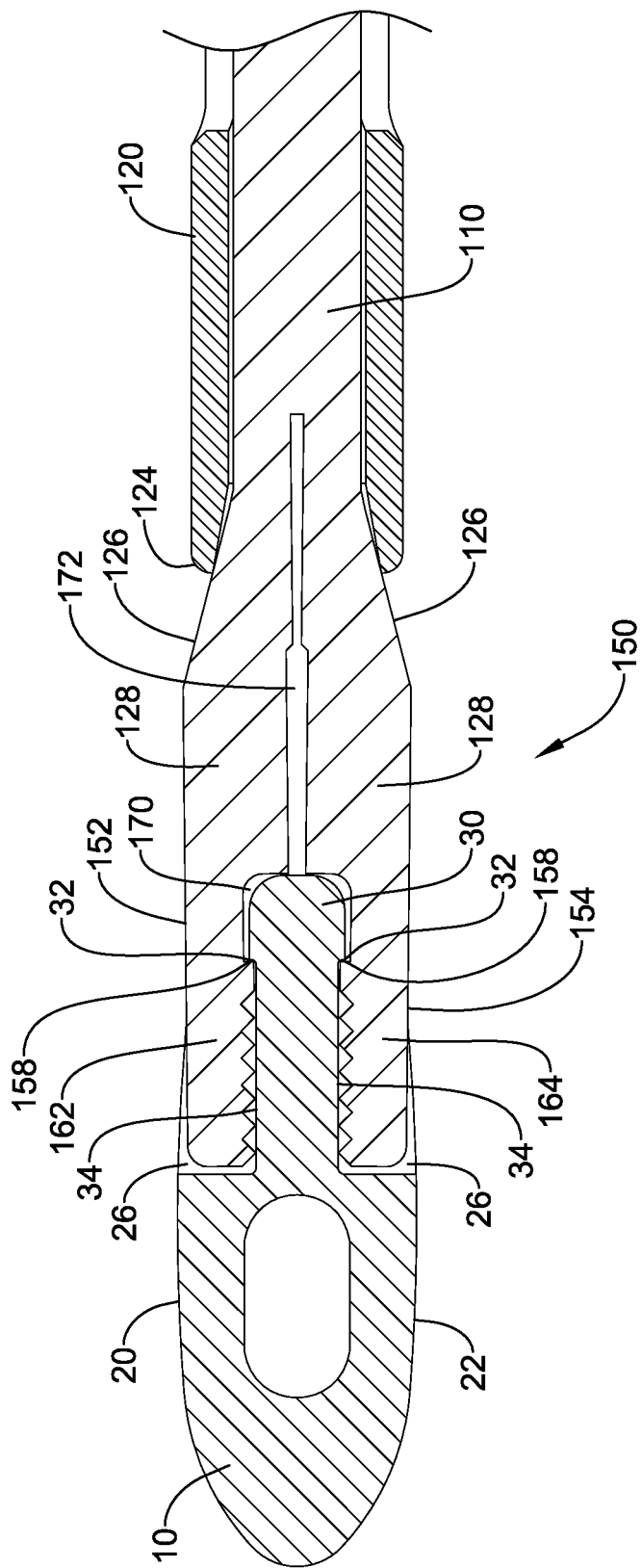
FIG. 8 is a cross-sectional view of the intervertebral implant being grasped by the insertion instrument.

FIGS. 7 and 8 illustrate interaction of the grasping mechanism 150 of the insertion instrument 100 with the trailing end portion of the intervertebral implant 10 for manipulating the implant 10 during insertion into a disc space between adjacent vertebrae. As shown in the figures, when coupled to the implant 10, the grasping portion 162 of the first jaw 152 may be positionable in the first channel 26 along the first side surface 20 of the intervertebral implant 10 and the grasping portion 164 of the second jaw 154 may be positionable in the second channel 26 along the second side surface 22 of the intervertebral implant 10. The engaging surface, which may include teeth or the like, of the first and second jaws 152, 154 may engage the base wall 34 of the channels 26 to grip the implant 10 therebetween.

With the grasping portions 162, 164 of the jaws 152, 154 positioned in the channels 26 and bearing against the base walls 34 of the channels 26, the positioning projection 30 of the implant 10 may be located in the enlarged opening 170 defined between the first jaw 152 and the second jaw 154. The arrangement of the implant 10 between the jaws 152, 154 may be such that the lips 158 of the jaws 152, 154 interact with the notches 32 of the implant 10 proximate the base of the positioning projection 30. Accordingly, the trailing end portion of the implant 10 may be locked between the jaws 152, 154 such that the implant 10 cannot be decoupled from the insertion instrument 100 until the jaws 152, 154 are permitted to be actuated outward a sufficient amount to allow the lips 158 of the jaws 152, 154 to disengage the notches 32 and pass around the positioning projection 30.

In using the insertion instrument 100 to insert the implant 10 during a medical procedure, the trailing end portion of the implant 10 may be positioned between the jaws 152, 154 of the grasping mechanism 150 while positioned in the released position shown in FIG. 6A. During coupling of the implant 10 with the insertion instrument 100, the jaws 152, 154 may deflect outward slightly to allow the positioning projection 30 to move into the enlarged opening 170 while the grasping portions 162, 164 of the first and second jaws 152, 154 are axially slid into the channels 26 formed in the side surfaces 20, 22 of the implant 10 from the trailing end of the implant 10. Once the positioning projection 30 is located in the enlarged opening 170, the knob 142 may be rotated to axially translate the inner shaft 110 (and thus the grasping mechanism 150) proximally relative to the outer shaft 120. As the inner shaft 110 and grasping mechanism 150 are actuated proximally, the distal end 124 of the outer shaft 120 may contact the tapered edges 126 of the jaws 152, 154 and urge the grasping portions 162, 164 toward each other, as described with FIG. 6B. Urging the grasping portions 162, 164 toward one another causes the engagement surfaces of the grasping portions 162, 164 to bear against the base walls 34 of the channels 26 to grip the implant 10 therebetween, while the lips 158 of the jaws 152, 154 interact with the notches 32 of the implant 10.

The insertion instrument 100 may then be manipulated by a user to move the implant 10 into proper position within the disc space between the adjacent vertebrae. If desired, a mallet or other striking tool may be used to apply a striking force against the striking plate 148 of the insertion instrument 100 during the insertion process. Once the implant 10 has been properly positioned within the disc space between the adjacent vertebrae, the knob 142 may be rotated in the opposite direction to axially translate the inner shaft 110 (and thus the grasping mechanism 150) distally relative to the outer shaft 120, and thus release the inward force against the jaws 152, 154 by the outer shaft 120. Once the jaws 152, 154 are free to deflect outward, the insertion instrument 100 may be decoupled from the trailing end portion of the implant 10 and withdrawn from the patient's body.

Those skilled in the art will recognize that aspects of the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. An assembly for installing an intervertebral implant between first and second vertebrae, the assembly comprising:
   i) an intervertebral implant including a leading end portion, a trailing end portion, a superior surface configured to engage a first vertebra, an inferior surface configured to engage a second vertebra, a first side surface, and a second side surface opposite the first side surface;
   the intervertebral implant including a first channel extending along the first side surface from a trailing end wall toward the leading end and a second channel extending along the second side surface from the trailing end wall toward the leading end;
   the intervertebral implant further including a positioning projection extending rearward from the trailing end wall;
   wherein the first channel has a base wall and the second channel has a base wall, wherein a width of the intervertebral implant between the base wall of the first channel and the base wall of the second channel is less than a width of the positioning projection;
   ii) an insertion instrument including an elongate shaft extending from a handle portion to a grasping mechanism configured to grasp the intervertebral implant;
   the grasping mechanism including first and second jaws configured to grasp the trailing end portion of the intervertebral implant therebetween;
   the first jaw including a grasping portion positionable in the first channel along the first side surface of the intervertebral implant and the second jaw including a grasping portion positionable in the second channel along the second side surface of the intervertebral implant, and
   the positioning projection positionable in an enlarged opening defined between the first jaw and the second jaw.

2. The assembly of claim 1, wherein the enlarged opening is between the grasping portions of the first and second jaws and a base portion of the first and second jaws.

3. The assembly of claim 1, wherein the enlarged opening has a width larger than a width measured between the grasping portions of the first and second jaws.

4. The assembly of claim 3, wherein a gap between the first jaw and the second jaw extends proximal of the enlarged opening.

5. The assembly of claim 4, wherein the gap has a width less than the width of the enlarged opening.

6. The assembly of claim 1, further comprising superior-inferior oriented notches located at a junction of the positioning projection and the first and second channels.

7. The assembly of claim 1, wherein the positioning projection extends from the superior surface to the inferior surface of the intervertebral implant.

8. An intervertebral implant, comprising:
   a leading end portion;
   a trailing end portion;
   a superior surface configured to engage a first vertebra;
   an inferior surface configured to engage a second vertebra;
   a first side surface;
   a second side surface opposite the first side surface;
   a first channel extending along the first side surface from a trailing end wall toward the leading end;
   a second channel extending along the second side surface from the trailing end wall toward the leading end; and
   a positioning projection extending rearward from the trailing end wall;
   wherein the first channel has a base wall and the second channel has a base wall, wherein a width of the intervertebral implant between the base wall of the first channel and the base wall of the second channel is less than a width of the positioning projection.

9. The intervertebral implant of claim 8, further comprising superior-inferior oriented notches located at a junction of the positioning projection and the first and second channels.

10. The intervertebral implant of claim 9, wherein the notches are located at a base of the positioning projection where the positioning projection extends from the trailing end wall.

* * * * *